United States Patent [19]

Koziol et al.

[11] Patent Number: 4,878,910
[45] Date of Patent: Nov. 7, 1989

[54] INTRAOCULAR LENS ASSEMBLY

[76] Inventors: Jeffrey E. Koziol, 1211 S. Arlington Heights Rd., Arlington Heights, Ill. 60005; Gholam A. Peyman, 123 Walnut St., New Orleans, La. 70118

[21] Appl. No.: 205,640
[22] Filed: Jun. 13, 1988
[51] Int. Cl.⁴ .............................................. A61F 2/16
[52] U.S. Cl. ........................................................ 623/6
[58] Field of Search ............................................. 623/6

[56] References Cited

U.S. PATENT DOCUMENTS

| | | | |
|---|---|---|---|
| 4,073,014 | 2/1978 | Poler | 623/6 |
| 4,159,546 | 7/1979 | Shearing | 623/6 |
| 4,242,760 | 1/1981 | Rainin | 623/6 |
| 4,573,998 | 3/1986 | Mazzocco | 623/6 |
| 4,608,049 | 8/1986 | Kelman | 623/6 |
| 4,615,702 | 10/1986 | Koziol et al. | 623/6 |
| 4,634,441 | 1/1987 | Clayman et al. | 623/6 |
| 4,657,546 | 4/1987 | Shearing | 623/6 |
| 4,702,865 | 10/1987 | Koziol et al. | 264/17 |

FOREIGN PATENT DOCUMENTS

| | | | |
|---|---|---|---|
| 3503690 | 11/1986 | Fed. Rep. of Germany | 623/6 |
| 2114315 | 8/1983 | United Kingdom | 623/6 |
| 2124500 | 2/1984 | United Kingdom | 623/6 |

Primary Examiner—Ronald L. Frinks
Attorney, Agent, or Firm—Roylance, Abrams, Berdo & Goodman

[57] ABSTRACT

An intraocular lens assembly used to replace the natural lens in the eye. The assembly comprises a preferably soft optical lens, a resilient housing having an aperture through which the lens can be inserted into or removed from the housing, and a resilient support comprising a central ring coupled to the housing and a pair of support arms extending outwardly from the ring. The assembly is readily foldable for insertion into the eye through a small incision, can support the soft optical lens without sagging and distortion, and allows the optical lens to be easily replaced.

26 Claims, 3 Drawing Sheets

U.S. Patent  Nov. 7, 1989  Sheet 3 of 3  4,878,910
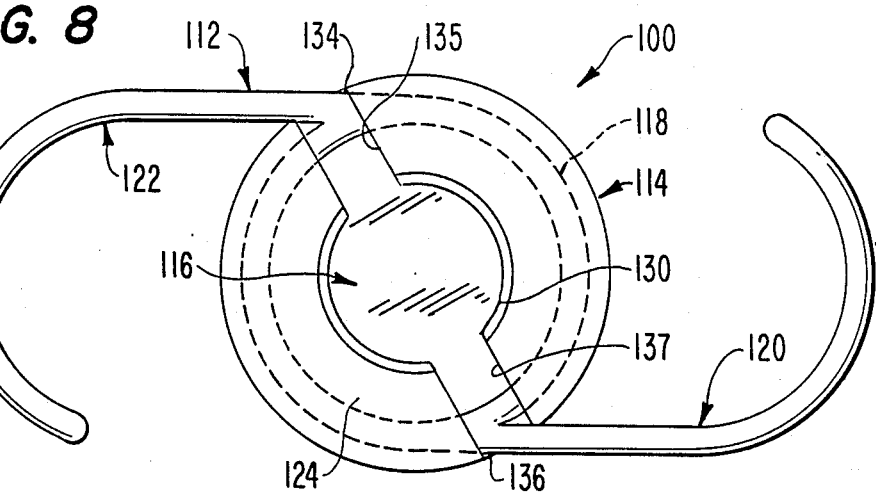
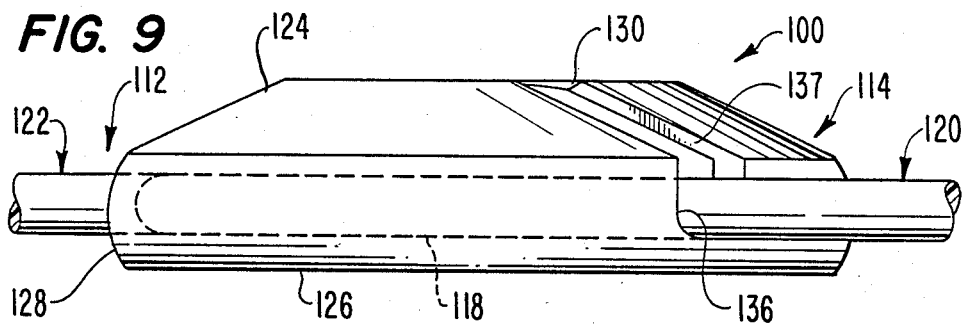
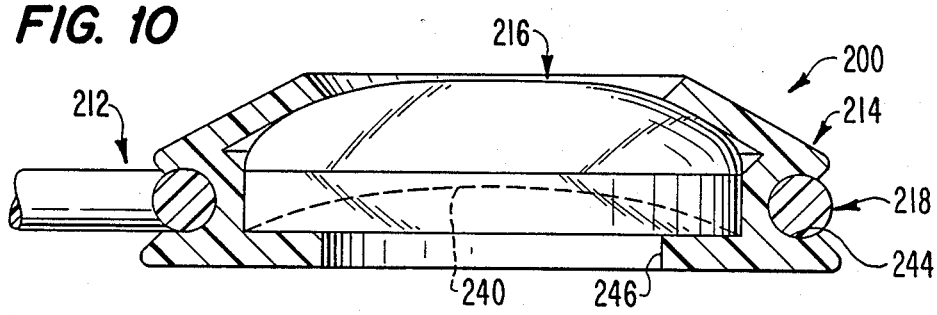
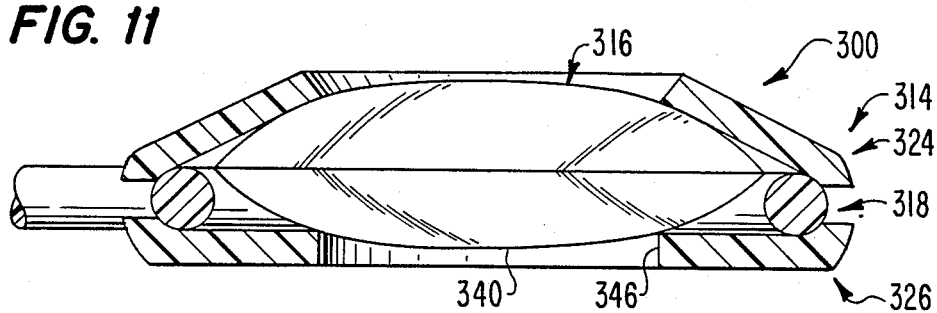

INTRAOCULAR LENS ASSEMBLY

FIELD OF THE INVENTION The invention relates to an intraocular lens assembly used to replace the natural lens in the eye. More particularly, the invention relates to an intraocular lens assembly that is readily foldable for insertion into the eye through a small incision, can support a soft optical lens without sagging and distortion, and allows the optical lens to be easily replaced.

BACKGROUND OF THE INVENTION

Artificial intraocular lenses, used to replace damaged or diseased natural lenses in the eye, have been widely used in the last several years. Typically, these artificial intraocular lenses comprise some type of optical lens and a support coupled to the lens for positioning the optical lens in the proper location in the eye.

These lenses have typically included hard polymeric or glass optical elements with metallic or polymeric supports. A significant problem with hard lenses is that the incision in the eye through which they are inserted must be at least as large as the diameter of the optical element of the lens. This can be up to six millimeters in length. Thus, the patient must experience a fairly traumatic large incision.

Soft, foldable polymeric lenses have been used but their acceptance has been hampered because it is difficult to support them without sagging and the resulting optical distortion, and it is difficult to insert them into the eye. U.S. Pat. Nos. 4,615,702 and 4,702,865 issued to the applicants herein do indeed disclose soft, foldable artificial polymeric lenses which resist sagging and distortion; however, they still require a relatively large incision, on the order of 4.0 to 4.5 millimeters.

Use of soft hydratable lenses, which are very hard when dry and soft after hydration, would be advantageous; however, it is difficult to support these lenses in the eye without sagging and distortion.

Another problem involving intraocular lenses is that they are typically not easily replaceable. Once installed, the tissue inside the eye tends to grow around the supporting structure and thus it is highly traumatic to remove the lens assembly. This would be exceptionally advantageous in both young and old people whose vision requirements vary as they grow older.

Thus, there is a continuing need for improvement in artificial intraocular lenses.

Examples of prior art intraocular lenses are disclosed in the following U.S. Pat. Nos. 4,073,014 to Poler; 4,159,546 to Shearing; 4,242,760 to Rainin; 4,573,998 to Mazzocco; and 4,615,702 and 4,702,865 to Koziol et al. Examples of prior intraocular lenses are also disclosed in United Kingdom patent application GB No. 2114315 A to Mazzocco, and United Kingdom patent application GB No. 2124500 A to Mazzocco.

SUMMARY OF THE INVENTION

Accordingly, a primary object of the invention is to provide an intraocular lens assembly which is relatively small and readily foldable for insertion into the eye through a relatively small incision.

Another object of the invention is to provide an intraocular lens assembly that can support a soft optical lens without sagging and optical distortion of the lens.

Another object of the invention is to provide an intraocular lens assembly that allows the optical lens to be easily replaced without significant trauma to the eye and without removal of the support structure.

A further object of the invention is to provide an intraocular lens assembly that can utilize a hydratable polymeric optical lens which can be readily supported inside the eye.

A further object of the invention is to provide an intraocular lens assembly in which the combination of an optical lens, a housing and a support can be inserted into the eye together or the combination of the housing and the support can be inserted together, with the optical lens then being added thereto.

The foregoing objects are basically attained by providing an intraocular lens assembly, the combination comprising an optical lens; a resilient housing having an anterior wall with an aperture therein and a posterior wall, the optical lens being received in the housing and located between the anterior and posterior walls; and a pair of support arms extending from the resilient housing.

Other objects, advantages and salient features of the invention will become apparent from the following detailed description, which, taken in conjunction with the annexed drawings, discloses preferred embodiments of the invention.

BRIEF DESCRIPTION OF THE DRAWINGS

Referring now to the drawings which form a part of this original disclosure:

FIG. 8 is a top plan view of a modified intraocular lens assembly which is similar to that shown in FIGS. 1-7 except that the housing has a pair of opposed slots therein;

FIG. 9 is an enlarged, fragmentary side elevational view of the modified intraocular lens assembly shown in FIG. 8;

FIG. 10 is a fragmentary side elevational view in transverse cross section of a second modified intraocular lens assembly which is similar to that shown in FIGS. 1-7 except that the ring is on the outside of the housing and the optical lens has a concave posterior surface; and FIG. 11 is a fragmentary side elevational view in transverse cross section of a third modified intraocular lens assembly which is similar to that shown in FIGS. 1–7 except that the housing is formed by two parts and the posterior surface of the optical lens is convex.

DETAILED DESCRIPTION OF THE INVENTION

Figure 1:
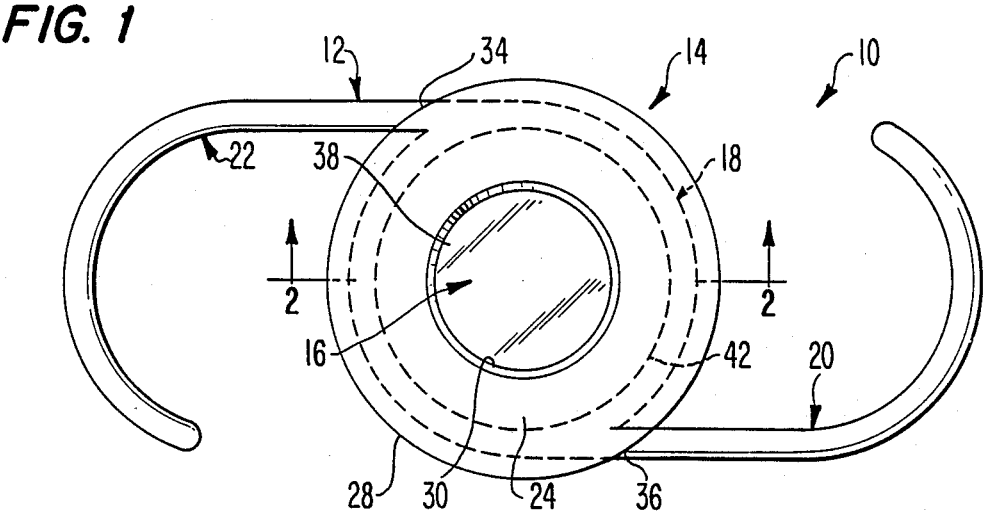
FIG. 1 is a top plan view of the intraocular lens assembly in accordance with the invention including the optical lens, housing and support.

Referring now to FIGS. 1–7, the intraocular lens assembly 10 in accordance with the invention comprises a support 12, a housing 14 coupled to the support, and an optical lens 16 received in and supported by the housing.

Support 12 is comprised of a central ring 18 and a pair of curved support arms 20 and 22 coupled to the ring and extending initially substantially tangentially therefrom. The ring and support arms are preferably substantially coplanar, have a uniform circular cross section, and are formed integrally from one piece of resilient polymeric material. This material can be, for example, tetrafluoroethylene, Dyacron, PMME, or a somewhat hard silicone. The material forming the support 12 is preferably somewhat stiffer than the material forming the housing, but is nonetheless foldable and resilient. In addition, this material preferably has a higher melting point so that the housing 14 can be molded around the support 12 as discussed in more detail hereinafter. The central ring 18 has a central axis that is coincident with the central axes of the housing and optical lens. These axes are preferably coincident with the optical axis in the eye of the patient who is receiving the intraocular lens assembly.

Figure 6:
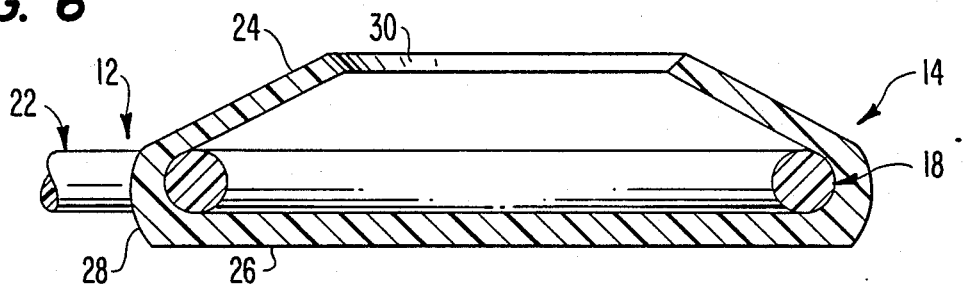
FIG. 6 is a fragmentary side elevational view in transverse section of the intraocular lens assembly shown in FIG. 5.

The housing 14 is circular in top plan view and is preferably formed of a resilient silicone which is transparent or semi-transparent to light. The housing is preferably formed integrally of one piece of material molded onto the ring in a manner similar to that disclosed in applicants' U.S. Pat. Nos. 4,615,702 and 4,702,865, the disclosures of which are hereby incorporated by reference. Thus, the ring is preformed with the arms coupled thereto and then the resulting support is placed in a hollow mold. The material forming the housing is then injected into the mold and is molded around the support as shown in FIG. 6 with the support arms extending outwardly therefrom.

The housing 14 as best seen in FIGS. 1, 2, 5 and 6 comprises an anterior wall 24, a posterior wall 26, and an annular member 28 interconnecting the outer peripheral edges of the anterior and posterior walls.

The anterior wall 24 is substantially frustoconical and tapers upwardly and inwardly at an angle of about 30°. This wall has a first central circular aperture 30 therein which has a diameter of about 3.0 to about 7.0 millimeters, preferably about 4.0 millimeters. This aperture is advantageously concentric to the central axis of the housing, support and optical lens.

The posterior wall 26 is preferably substantially planar and about 0.10 millimeter thick. It extends substantially perpendicular to the longitudinal axis of the housing.

The annular member 28 is substantially cylindrical, has an inner diameter of about 6.0 to about 8.0 millimeters and interconnects the anterior and posterior walls, preferably by being integrally formed therewith. The annular member has a pair of diametrically opposed openings 34 and 36 seen in FIGS. 1 and 5 through which the support arms 20 and 22, respectively, extend.

Figure 2:
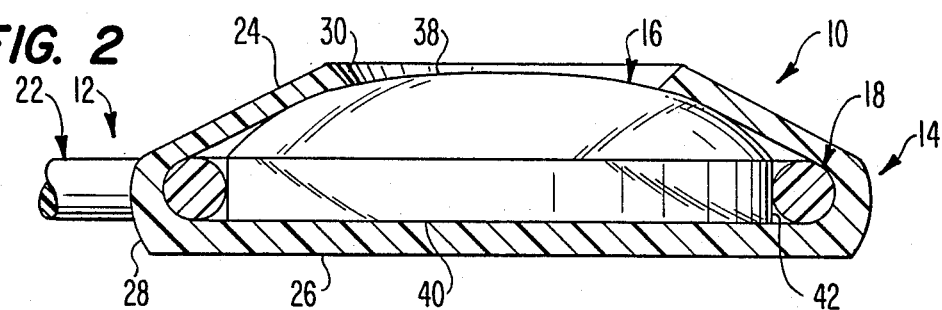
FIG. 2 is an enlarged, fragmentary side elevational view in section of the intraocular lens assembly shown in FIG. 1 taken along line 2—2 in FIG. 1.
Figure 3:
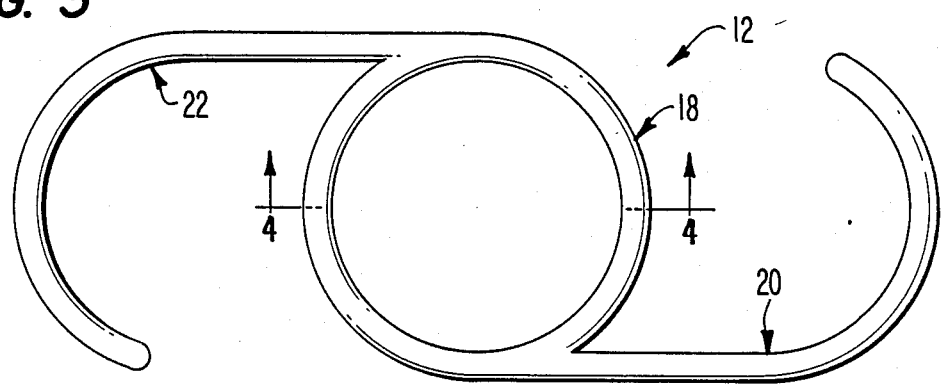
FIG. 3 is a top plan view of the support shown in FIGS. 1 and 2 comprising a central ring and a pair of support arms.
Figure 4:
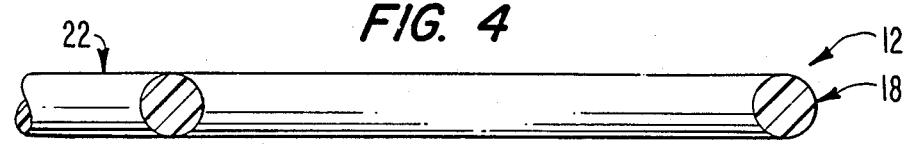
FIG. 4 is an enlarged, fragmentary side elevational view in section of the support shown in FIG. 3 taken along line 4—4 in FIG. 3.
Figure 5:
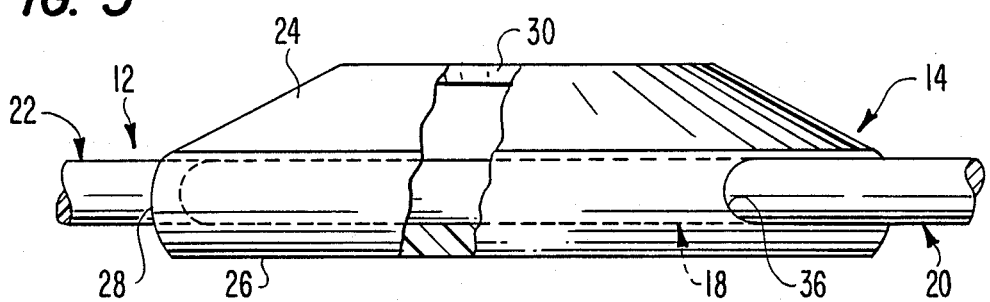
FIG. 5 is an enlarged, fragmentary side elevational view of the intraocular lens assembly shown in FIG. 1 with a portion of the housing broken away to show the inside thereof and with the optical lens removed for clarity.

As seen best in FIGS. 2, 5 and 6, he central ring 18 on the support engages the inside surface of the annular member 28 as well as the inside surfaces of the anterior wall 24 and posterior wall 26. This provides essentially a skeleton and structural support for the resilient housing 14 to prevent it from sagging and to provide it with a continuous annular configuration. The support arms 20 and 22 extend through the openings 34 and 36 outwardly and away from the housing and are engaged with various tissue inside the eye to provide support to the intraocular lens assembly in the correct orientation inside the eye. The combination of the annular member 28 and the ring 18 form a side wall of the housing, which encircles the optical lens 16 as seen in FIG. 2.

Figure 7:
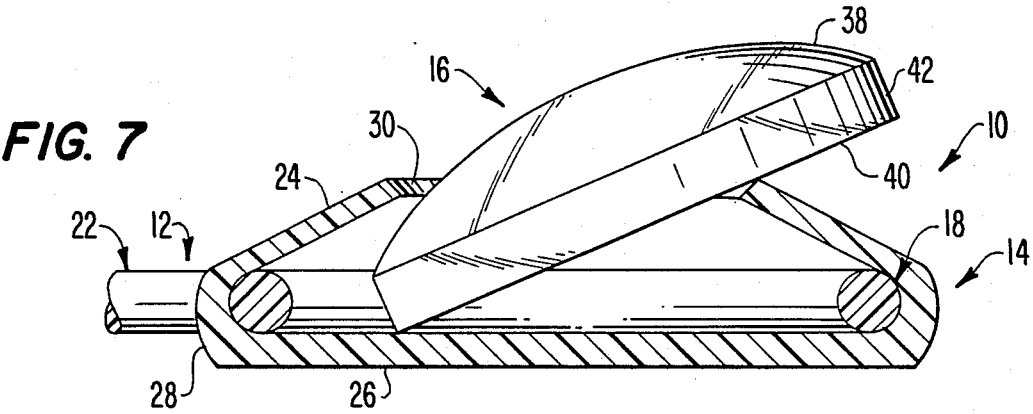
FIG. 7 is a fragmentary side elevational view in transverse section similar to that shown in FIG. 6 except that the optical lens is being inserted into the housing via the aperture therein.

The optical lens 16 seen in FIGS. 1, 2 and 7, is preferably formed from a soft polymeric material and preferably a hydrogel material that is hard when dry and soft and jellylike when hydrated. Examples of this type of lens are those referred to as Xerogel and HEMA. As seen in FIGS. 1, 2 and 7, the optical lens 16 is plano-convex and has a longitudinal axis aligned with the longitudinal axes of the housing and the support. The lens comprises an anterior surface 38 which is convex, a posterior surface 40 which is substantially planar, and a cylindrical side surface 42 interconnecting the anterior and posterior surfaces. The overall height of the optical lens is advantageously about 1.0 millimeter and the outer diameter is advantageously about 6.0 to about 8.0 millimeters. The optical lens can also be convex-concave as seen in FIG. 10, bi-convex as seen in FIG. 11, or any other lenticular shape.

The optical lens as seen in FIG. 7 can be inserted into or removed from housing 14 via stretching aperture 30 in the housing. Once inserted as seen in FIGS. 1 and 2, the side surface 42 of the lens engages the inner surface of ring 18, the anterior surface 38 of the lens engages the anterior wall 24 of the housing, and the posterior surface 40 of the lens engages the inside surface of posterior wall 26 on the housing. Due to this positioning and support, the soft lens tends not to sag and its optical properties are not distorted.

In installing the intraocular lens assembly 10 in accordance with the invention, advantageously the combination of the support 12 and housing 14 can be inserted together through a small incision in the eye on the order of about 2.5 to about 3.0 millimeters. This is done by making the incision, folding the assembly 10, inserting it through the incision, and then unfolding it and attaching it in the proper orientation in the eye. Then, the optical lens 16 can be maneuvered through the incision and inserted into the housing as shown in FIG. 7. The optical lens 16 can be inserted in its hard unhydrated form or in its soft hydrated form. Alternatively, the optical lens can be hydrated, inserted into the housing, and then the combined lens, housing and support can be folded and inserted into the eye.

In all events, this results in an intraocular lens assembly that is readily foldable for insertion into the eye through a small incision, that can support a soft optical lens without sagging or distortion, and allows the optical lens to be easily replaced. Optical lens 16 can be replaced by making a new incision into the eye, removing the original optical lens from the housing 14 and the eye via the incision, and then placing a new optical lens into the housing via the incision.

EMBODIMENT OF FIGS. 8 AND 9

A modified intraocular lens assembly 100 is shown in FIGS. 8 and 9 which is substantially the same as intraocular lens assembly 10 shown in FIGS. 1–7, except that housing 114 has a pair of radial slots 135 and 137 communicating with openings 134 and 136 in the housing. The remaining parts of the assembly 100 are the same as those shown in FIGS. 1-7 and are given similar reference numerals preceded by 100.

By utilizing these radial slots, the housing 114 can be separately molded and then coupled to the support 112 by insertion of central ring 118 therein. In this embodiment, the support arms 120 and 122 would still extend outwardly via openings 134 and 136 which extend into slots 135 and 137. As seen in FIG. 8, slots 135 and 137 are formed in the anterior wall 124 and extend to the aperture 130 in the anterior wall.

EMBODIMENT OF FIG. 10

A further modified intraocular lens assembly 200 is shown in FIG. 10 which is the same as that shown in FIGS. 1-7, except for basically three differences. Assembly 200 comprises a support 212 having a central ring 218 and support arms similar to that shown in FIG. 1, a housing 214 and an optical lens 216.

Optical lens 216 is the same as optical lens 16 in FIG. 1 except that its posterior surface 240 is concave.

In this embodiment of FIG. 10, ring 218 in support 212 is outside the housing 214 and is received in a groove 244 formed on the outer periphery of the housing annular member. In this case, openings for the support arms are unnecessary.

Housing 214 also has a second aperture 246 in its posterior wall to provided added flexibility to the housing. Although lens 16 shown in FIG. 1 is plano-convex, it could be in the convex-concave shape shown in FIG. 10 by lens 216.

EMBODIMENT OF FIG. 11

A further modified intraocular lens assembly 300 is shown in FIG. 11 which is the same as that shown in FIGS. 1-7 except for three differences.

First, lens 316 has a convex posterior surface 340, which could be used in the embodiments of FIGS. 1-7, 8-9 or 10 as well.

Second, the housing 314 is formed in two parts including a separate anterior wall 324 and a separate posterior wall 326, with central ring 318 in the support forming the annular member and side wall interconnecting the walls 324 and 326. These walls are preferably adhered to ring 318 by any suitable adhesive. This construction would use less material in the housing and would provide more flexible posterior and anterior walls.

The third difference is the use of the second aperture 346 in the posterior wall 326 for added flexibility and less material.

While various advantageous embodiments have been chosen to illustrate the invention, it will be understood by those skilled in the art that various changes and modifications can be made therein without departing from the scope of the invention as defined in the appended claims.

What is claimed is:

1. An intraocular lens assembly, the combination comprising:
   an optical lens formed of a soft material;
   a resilient housing having an anterior wall with an aperture therein and a posterior wall, said optical lens being received in said housing and located between said anterior and posterior walls; and
   a pair of support arms extending from said resilient housing,
   said pair of support arms extending into said housing.

2. An assembly according to claim 1, wherein said optical lens is formed from hydrogel material.

3. An assembly according to claim 1, wherein said housing further comprises an annular side wall interconnecting said anterior and posterior walls.

4. An assembly according to claim 1, wherein said anterior wall is substantially frustoconical.

5. An assembly according to claim 4, wherein said posterior wall is substantially planar.

6. An assembly according to claim 1, wherein said posterior wall is substantially planar.

7. An assembly according to claim 1, wherein said housing includes a ring encircling said optical lens.

8. An assembly according to claim 1, wherein
   said housing is integrally formed of one piece of material.

9. An assembly according to claim 8, wherein
   said material is silicone.

10. An assembly according to claim 1, wherein said housing further comprises a ring interconnecting said anterior and posterior walls.

11. An assembly according to claim 1, wherein said housing further comprises a ring, said arms being coupled to said ring.

12. An assembly according to claim 1, wherein said posterior wall has a second aperture therein.

13. An assembly according to claim 1, wherein said housing is formed of material that is at least partially transparent.

14. An assembly according to claim 1, wherein said housing is formed of silicone.

15. An intraocular lens assembly, the combination comprising:
   an optical lens formed of a soft material;
   a resilient housing having an anterior wall with an aperture therein and a posterior wall, said optical lens being received in said housing and located between said anterior and posterior walls; and
   a pair of support arms extending from said resilient housing,
   said housing further comprising an annular side wall including an annular member interconnecting said anterior and posterior walls, and a ring encircling the outermost perimeter of said optical lens.

16. An assembly according to claim 15, wherein
   said ring is located inside said annular member.

17. An assembly according to claim 15, wherein
   said ring is located outside said annular member.

18. An intraocular lens assembly, the combination comprising:
   an optical lens formed of a soft material;
   a resilient housing having an anterior wall with an aperture therein and a posterior wall, said optical lens being received in said housing and located between said anterior and posterior walls; and
   a pair of support arms extending from said resilient housing,
   said anterior wall having a pair of slots therein communicating with said aperture, each of said support arms being received in one of said slots.

19. An intraocular lens assembly, the combination comprising:
   an optical lens;
   a resilient housing having an anterior wall with an aperture therein and a posterior wall, said optical lens being received in said housing and located between said anterior and posterior walls;

a resilient ring coupled to said housing and encircling said optical lens; and a pair of support arms coupled to said ring and extending from said ring outwards from said housing.

20. An assembly according to claim 19, wherein said ring and support arms are integrally formed of one piece of material.

21. An assembly according to claim 19, wherein said optical lens is formed from hydrogel material.

22. An assembly according to claim 19, wherein said housing further comprises an annular member interconnecting said anterior and posterior walls, said ring engaging said annular member.

23. An assembly according to claim 19, wherein said optical lens is formed of a soft material.

24. An intraocular lens assembly, the combination comprising:

an optical lens;

a resilient housing having an anterior wall with an aperture therein and a posterior wall, said optical lens being received in said housing and located between said anterior and posterior walls; and a pair of support arms extending from said resilient housing, said pair of support arms extending into said housing.

25. An intraocular lens assembly, the combination comprising:

an optical lens;

a resilient housing having an anterior wall with an aperture therein and a posterior wall, said optical lens being received in said housing and located between said anterior and posterior walls; and a pair of support arms extending from said resilient housing, said housing further comprising an annular side wall including an annular member interconnecting said anterior and posterior walls, and a ring encircling the outermost perimeter of said optical lens.

26. An intraocular lens assembly, the combination comprising:

an optical lens;

a resilient housing having an anterior wall with an aperture therein and a posterior wall, said optical lens being received in said housing and located between said anterior and posterior walls; and a pair of support arms extending from said resilient housing, said anterior wall having a pair of slots therein communicating with said aperture, each of said support arms being received in one of said slots.

* * * * *